United States Patent [19]  [11] 4,048,210
Davis  [45] Sept. 13, 1977

[54] TRANSCYANOHYDRINATION
[75] Inventor: Royston H. Davis, Rainham, England
[73] Assignee: Shell Oil Company, Houston, Tex.
[21] Appl. No.: 692,180
[22] Filed: June 2, 1976
[30] Foreign Application Priority Data
June 11, 1975 United Kingdom ............... 25017/75
[51] Int. Cl.$^2$ .................. C07C 120/00; C07C 121/66
[52] U.S. Cl. ................................. 260/465 F
[58] Field of Search ............................. 260/465 F
[56] References Cited
U.S. PATENT DOCUMENTS 3,377,155  4/1968  Well et al. .................. 260/465 F X
3,489,785  1/1970  Kurono et al. .................. 260/465 F
3,787,477  1/1974  Matthews ......................... 260/465 F

OTHER PUBLICATIONS

Migrdichiaa, "The Chemistry of Organic Cyanogen Compounds", 1947, Reinhold Pub. Corp., pp. 173–176.

Primary Examiner—Joseph Paul Brust
Assistant Examiner—Robert C. Whittenbaugh

[57] ABSTRACT

A process for converting water insoluble aldehydes to cyanohydrins by reacting the cyanohydrin of a ketone with the water insoluble aldehyde in an inert organic solvent in the presence of an organic base is described.

7 Claims, No Drawings

TRANSCYANOHYDRINATION

BACKGROUND OF THE INVENTION

1. Field of the Invention

The present invention relates to a process for the preparation of certain benzyl alcohol derivatives which can be used as or suitably converted into intermediates used in the preparation of biologically, especially insecticidally, active compounds.

It has been found that compounds of the general formula:

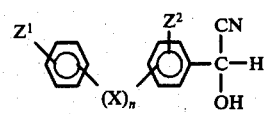

(I)

wherein n is 0 or 1 and X represents an oxygen or a sulphur atom or an alkylene group; Z and $Z^1$ each represents independently hydrogen or one or more halogen, alkyl, alkenyl, haloalkyl, alkoxy, aryl, cyano or nitro groups, can be prepared in almost quantitative yields by reacting the corresponding benzaldehyde derivative with a ketocyanohydrin in an inert organic solvent in the presence of an organic base.

Thus, the present invention relates to a process for the preparation of alpha-cyano benzylalcohol derivatives of the general formula (I) by reacting a benzaldehyde derivative of the general formula:

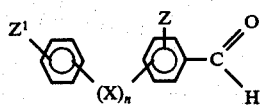

(II)

with a ketocyanohydrin of the general formula:

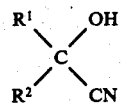

(III)

in an inert organic solvent in the presence of an organic base, in which formulae n, X, Z and $Z^1$ are as hereinbefore defined and $R^1$ and $R^2$ each represents a substituted or unsubstituted hydrocarbyl group, or $R^1$ and $R^2$ together represent an alkylene group.

The process according to the present invention relates in particular to the preparation of meta-aryloxy-alpha cyano benzyl alcohol derivatives, especially to meta-phenoxy-alpha cyano benzyl alcohol, by reacting the corresponding meta-aryloxy benzaldehyde, especially metaphenoxy benzaldehyde, with a ketocyanohydrin, especially acetone cyanohydrin, in an organic solvent in the presence of an organic base.

BACKGROUND OF THE INVENTION

The interchange between an aldehyde or a ketone and a ketocyanohydrin, is readily known for the synthesis of lower, water-soluble cyanohydrins such as acetaldehyde cyanohydrin. This method has the advantage of avoiding the handling of anhydrous hydrogen cyanide. Reasonable yields can be obtained by continuously distilling off the low boiling ketone obtained when reacting an aqueous solution of the starting cyanohydrin with the appropriate aldehyde or ketone.

The benzaldehyde derivatives with the general formula II are immiscible with water, however, and application of the above-mentioned procedure using such compounds would only lead to low yields.

It has now been found that an almost quantitative conversion of benzaldehyde derivatives according to the general formula II into the corresponding cyano benzyl alcohol derivatives can be achieved when the reaction, to be referred to hereinafter as transcyanohydrination, is carried out in an organic solvent in the presence of an organic base. The cyano benzyl alcohol derivatives are obtained in very high yields, usually exceeding 95%. It has moreover been found that it is not necessary to remove (continuously) the ketone formed during the production of the cyano benzyl alcohol derivative in order to obtain a good yield. The process according to the present invention is also advantageous in that any starting ketocyanohydrin left in the reaction mixture can be easily removed, together with the ketone formed during the working-up procedure, for instance, by washing the reaction mixture with an aqueous acid solution.

The meta-aryloxy-alpha-cyano benzyl alcohol derivatives are valuable intermediates in the preparation of pesticides containing a (substituted) meta-aryloxy benzyl group. They can be suitably used, for example, in the preparation of esters of cyclopropane carboxylic acids or phenyl acetic acids which possess interesting insecticidal properties, by reacting them, either as such or after having converted them into the corresponding meta-aryloxy-alpha cyano benzyl halides or -tosylates, with the appropriate cyclopropane carboxylic acid or phenyl acetic acid or acid derivative.

SUMMARY OF THE INVENTION

Cyanohydrin of the formula

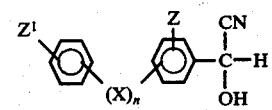

wherein X is an oxygen or sulfur atom, n is equal to 0 or 1 and Z and $Z^1$ are independently hydrogen or one or more halogen, alkyl, alkenyl, haloalkyl, alkoxy, aryl; cyano or nitro group are produced by contacting a water-insoluble aldehyde of the formula

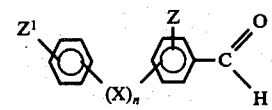

where X, Z, $Z^1$ and n are defined as above, with a ketocyanohydrin of the formula

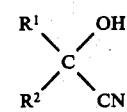

where $R^1$ and $R^2$ are substituted or unsubstituted hydrocarbyl groups or $R^1$ and $R^2$ together represent an alkylene group, in an inert organic solvent in the presence of an organic base. The cyanohydrin exchange may be aided by displacing the equilibrium by either having a molar excess of the ketocyanohydrin or by selectively distilling the ketone from the reaction or by both.

DESCRIPTION OF THE PREFERRED EMBODIMENTS

Benzaldehyde derivatives according to the general formula II which can be suitably used as starting materials in the process according to the present invention comprise those wherein $n = 1$, X represents oxygen and Z and $Z^1$ each represents a hydrogen atom or one or more chlorine atoms or an alkyl or alkoxy group having up to 6 carbon atoms, and when $n = 0$, those wherein Z represents one or more halogen atoms or one or more alkyl or alkenyl groups having up to 6 carbon atoms. Preference is given to the use of benzaldehyde derivatives according to the general formula II wherein $n = 1$, X represents oxygen and Z and $Z^1$ each represents hydrogen, chlorine, methyl or methoxy. Most preference is given to the use of meta-phenoxy benzaldehyde as a starting material. Examples of suitable starting materials wherein $n = 0$ comprise pentachlorobenzaldehyde and 2,6-dimethyl-4-allyl benzaldehyde.

These benzaldehydes are substantially water-insoluble, i.e., less than 0.1 mole dissolves in 1 liter of water at 20° C, preferably less than 0.05 moles and most preferably less than 0.01 moles.

The ketocyanohydrins according to the general formula III which can be suitably used in the process according to the present invention comprise those wherein $R^1$ and $R^2$ each represents an alkyl group, especially an alkyl group having 1 to 6 carbon atoms inclusive. The preferred acyclic cyanohydrins are those formed from acetone, diethylketone and methylethylketone. Good results have been obtained using acetone cyanohydrin as the cyano-transfer agent.

The groups $R^1$ and $R^2$ may contain one or more inert substituents but these are not essential for the course of the reaction. $R^1$ and $R^2$ may form a single alkylene group, i.e., where $R^1$, $R^2$ together with the carbon attached to the cyano and hydroxyl group form a ring. The preferred alkylene groups are those which form part of a 5 or 6 membered ring. The preferred cyclic cyanohydrin is that derived from cyclohexanone.

The ketocyanohydrins to be reacted with the benzaldehyde derivatives of the general formula II can be easily prepared by reacting the appropriate ketone with aqueous hydrogen cyanide (or a cyanide and an inorganic acid in aqueous solutions). Suitably an excess of ketone can be applied which serves as a solvent for the ketocyanohydrin under the reaction conditions. In order to improve the yield of the process according to the present invention the ketocyanohydrin should be distilled immediately prior to use. By immediately it is meant within 2 hrs, preferably 1 hr and most preferably within 10 mins. of use in the process.

As already stated hereinbefore the process according to the present invention has to be carried out in the presence of an inert organic solvent in order to dissolve, or at least to disperse homogeneously the benzaldehyde derivative in the reaction medium. Suitable solvents comprise benzene, toluene, the xylenes, as well as hydrocarbons such as pentane, hexane, heptane, octane and halogenated, especially chlorinated hydrocarbons such as methylene chloride, chloroform, carbon tetrachloride, dichloroethane and chlorobenzene. Also ethers and cyclic ethers can be suitably used.

The process according to the present invention has to be carried out in the presence of an organic base. Preference is given to the use of organic nitrogen-bases such as amines, in particular tertiary amines such as trimethylamine, triethylamine and tri-n-butylamine. The preferred tertiary amine is triethylamine. Also pyridine and its homologues can be suitably used. The use of inorganic bases lead to the production of relatively large amounts of benzoin condensation type products as these bases are able to generate cyanide-ions which strongly catalyze benzoin-condensations.

The transcyanohydrination is advantageously carried out using an excess of ketocyanohydrin. Good results have been obtained using a molar ratio ketocyanohydrin/benzaldehyde derivative of above 1, between about 1 to about 15, preferably above 1.5 between about 1.5 and about 10 and most preferably above 3, between about 3 and about 5. However, reasonable yields can be obtained using a stoichiometric amount of the reactants.

The amount of catalyst to be used can vary within wide limits. Normally, amounts of from 5-50% wt, calculated on ketocyanohydrin, can be suitably applied. It has been found that less catalyst is required when a freshly distilled ketocyanohydrin is used. Preference is given to amounts of catalysts in the range of from 10-25% wt, calculated on ketocyanohydrin.

The process according to the present invention is carried out at a moderate temperature, for example, between 0° and 50° C although temperatures outside this range are not excluded. Good results can be obtained using ambient temperature. Although the reaction is normally carried out at autogeneous pressure, pressures up to 10 atmospheres can be readily applied.

The reaction time can range from about 10 min. to 24 hrs, preferably 0.5 hrs to 5 hrs and most preferably 0.5 hrs to 2 hrs.

The (excess) ketocyanohydrin normally present in the reaction mixture can be easily removed in the working-up procedure by washing the reaction mixture with an aqueous acid solution, preferably aqueous sulfurous acid. It has been found advantageous to introduce sulfur dioxide gas in the reaction mixture prior to washing with an aqueous acid solution in order to prevent decomposition of the product formed. The product can be obtained by evaporating the inert organic solvent.

The process may be carried out in a batch or continuous mode. The continuous mode can be a stepwise addition process or one in which reactants and products are continuously added and withdrawn.

The compounds according to the general formula I are valuable intermediates, especially in the preparation of compounds of the general formula IV:

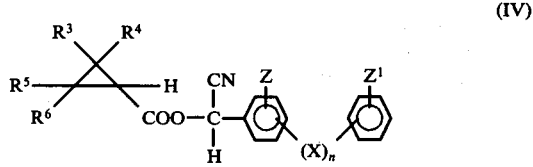

(IV)

wherein n, X, Z and $Z^1$ are as defined hereinbefore and $R^3$, $R^4$, $R^5$ and $R^6$ each represents hydrogen, halogen, alkyl, haloalkyl, alkenyl, haloalkenyl or aryl or $R^3$ and $R^4$ or $R^5$ and $R^6$ may together form an alkylene group. The present invention therefore also relates to a process for the preparation of compounds of the general formula IV by reacting a compound of the general formula I with a cyclopropane carboxylic acid halide having the substituents $R^3$, $R^4$, $R^5$ and $R^6$ as defined hereinbefore or by converting a compound of the general formula I into the corresponding halide which is then reacted with a cyclopropane carboxylic acid having the substituents $R^3$, $R^4$, $R^5$ and $R^6$ as defined hereinbefore.

The invention is illustrated by, but by no means limited to, the following Illustrative Embodiments.

ILLUSTRATIVE EMBODIMENT I

To a solution of 4.5 g 3-(4'-methoxyphenoxy) benzaldehyde (0.02 mole) and 3.4 g acetone cyanohydrin (0.04 mole) in 100 ml sieve-dried carbon tetrachloride was added under stirring at room temperature 2 ml triethylamine (about 0.02 mole) in a single portion. After stirring at room temperature during 1 hour, proton magnetic resonance measurement indicated a reduction of about 50% in the acetone cyanohydrin content together with removal of the benzaldehyde proton at $\delta$ 9.9 (in CDCl3).

Gaseous sulfur dioxide was bubbled through the reaction mixture which was then washed three times with 150 ml portion of aqueous sulfurous acid (pH about 2). The carbontetrachloride layer was dried over magnesium sulfate. 3-(4'-methoxy-phenoxy) alpha-cyano benzyl alcohol was obtained almost quantitatively after removal of carbon tetrachloride under reduced pressure at 0° C.

ILLUSTRATIVE EMBODIMENT II

To a solution of 1.98 g m-phenoxybenzaldehyde (0.01 mole) and 1.7 g acetone cyanohydrin (0.02 mole) in 20 ml carbontetrachloride was added 0.5 ml of triethylamine (about 0.005 mole). The solution was allowed to stand at 20° C for 1 hour.

Gaseous sulfur dioxide was bubbled through the reaction mixture during 1 minute. The excess acetone cyanohydrin was removed by washing two times with 20 ml aqueous sulfurous acid (pH about 2.7). The carbontetrachloride layer was dried over magnesium sulfate and carbontetrachloride removed under reduced pressure (0.8 mm Hg) at 0° C. The product formed almost in a quantitative yield contained 98.3% metaphenoxy-alpha cyano benzyl alcohol and 1.7% meta-phenoxy benzaldehyde (p.m.r. analysis).

ILLUSTRATIVE EMBODIMENT III

The following Illustrative Embodiment shows the reduced yields obtained with the convention transcyanohydrination process when applied to water insoluble aldehydes.

1.98 g m-phenoxybenzaldehyde (0.01 mole) was added to 3.4 g acetone cyanohydrin (0.04 mole) in 20 ml water. 0.25 g triethylamine 0.0025 mole) was added at 20° C to the vigorously stirred heterogenous mixture.

Proton magnetic resonance measurement demonstrated that the organic phase after 1 hour contained only 10% of m-phenoxy-alpha cyano benzylalcohol and 80% unconverted m-phenoxybenzaldehyde. A further 0.25 g of triethylamine was added while vigorously stirring the reaction mixture. After 1 hour the organic phase contained 15% of meta-phenoxyalpha cyanobenzylalcohol (p.m.r. $\delta$5.45 (hydroxyl proton), $\delta$3.85 (1H)) and 70% unconverted m-phenoxybenzaldehyde ($\delta$ 9.95).

I claim as my invention:

1. A process for making cyanohydrins having the formula:

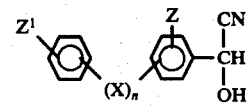

where $n$ is an integer between 0 and 1 inclusive, X is an oxygen or sulfur atom, Z and $Z^1$ each are independently hydrogen, alkyl, alkenyl, haloalkyl, alkoxy, aryl, cyano or nitro groups having up to 6 carbon atoms which comprises contacting at a temperature between 0° and 50° C at pressures up to 10 atmospheres and for a time ranging from about 10 minutes to about 24 hours a substantially water-insoluble aldehyde having the formula:

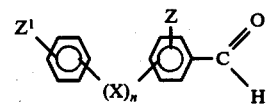

where $n$, X, Z and $Z^1$ are defined as above with a ketocyanohydrin having the formula:

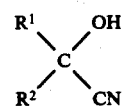

where $R^1$ and $R^2$ are alkyl groups having 1 to 6 carbon atoms or $R^1$ and $R^2$ together are a 5 or 6 membered alkylene group, in an inert organic solvent in the presence of an organic nitrogen-base wherein the molar ratio of ketocyanohydrin to aldehyde is between about 1 to about 15 and the base is present in an amount equal to about 5 to 50 wt percent based on the ketocyanohydrin.

2. The process of claim 1 where the aldehyde is meta-phenoxybenzaldehyde.

3. The process of claim 2 where the ketocyanohydrin is the cyanohydrin of a ketone selected from the group consisting of acetone, methylethylketone, diethyl ketone, and cyclohexanone.

4. The process of claim 3 where the inert organic solvent is selected from the group consisting of benzene, toluene, xylene, pentane, hexane, heptane, octane, methylene chloride, chloroform, carbon tetrachloride, dichloroethane and chlorobenzene.

5. The process of claim 4 where the organic base is selected from the group consisting of trimethylamine, triethylamine, tri-n-butylamine and pyridine.

6. The process of claim 5 wherein the ketocyanohydrin is distilled immediately before being used in the process.

7. The process of claim 6 wherein $R^1$ and $R^2$ are methyl groups and where the product is isolated by bubbling in $SO_2$, washing with aqueous acid solution, drying the organic solution of product and fractionally distilling.

* * * * *